(12) United States Patent
Chang et al.

(10) Patent No.: US 10,280,427 B2
(45) Date of Patent: May 7, 2019

(54) MODULAR SYNTHETIC GAL1 PROMOTER AND USE THEREOF

(71) Applicant: Nanyang Technological University, Singapore (SG)

(72) Inventors: Matthew Wook Chang, Singapore (SG); Wei Suong Teo, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 0 days.

(21) Appl. No.: 14/889,755

(22) PCT Filed: Jan. 20, 2014

(86) PCT No.: PCT/SG2014/000021
§ 371 (c)(1),
(2) Date: Nov. 6, 2015

(87) PCT Pub. No.: WO2014/182242
PCT Pub. Date: Nov. 13, 2014

(65) Prior Publication Data
US 2016/0108410 A1    Apr. 21, 2016

Related U.S. Application Data

(60) Provisional application No. 61/820,860, filed on May 8, 2013.

(51) Int. Cl.
| | | |
|---|---|---|
| *C12N 15/81* | (2006.01) | |
| *C12N 15/63* | (2006.01) | |
| *C12P 21/00* | (2006.01) | |

(52) U.S. Cl.
CPC .......... *C12N 15/81* (2013.01); *C12N 15/635* (2013.01); *C12P 21/00* (2013.01)

(58) Field of Classification Search
None
See application file for complete search history.

(56) References Cited

PUBLICATIONS

DiRusso et al., J. Biol. Chem., 267, 12:8685-8691, 1992).*
Blake et al., "Phenotypic Consequences of Promoter-Mediated Transcriptional Noise," *Molecular Cell* 24:853-865 (Dec. 28, 2006).
Blake et al., "Noise in eukaryotic gene expression," *Nature* 422:633-637 (Apr. 10, 2003).
Blazeck et al., "Controlling Promoter Strength and Regulation in *Saccharomyces cerevisiae* Using Synthetic Hybrid Promoters," *Biotechnology and Bioengineering* 109(11):2884-2895 (Nov. 2012).
Blazeck et al., "Promoter engineering: Recent advances in controlling transcription at the most fundamental level," *Biotechnology Journal* 8:46-58 (2013).
Chen et al., "Transporter engineering for improved tolerance against alkane biofuels in *Saccharomyces cerevisiae*," *Biotechnology for Biofuels* 6:21 (10 pages) (2013).
Ellis et al., "Diversity-based, model-guided construction of synthetic gene networks with predicted functions," *Nature Biotechnology* 27(5):465-471 (May 2009).
Hallenbeck, "Chapter 12—Microbial Production of Fatty-Acid-Based Biofuels," *Microbial Technologies in Advanced Biofuels Production*, DOI 10.1007/978-1-4614-1208-3_12, © Springer Science +Business Media, LLC (18 pages) (2012).
Holtz et al., "Engineering Static and Dynamic Control of Synthetic Pathways," *Cell* 140:19-23 (Jan. 8, 2010).
Jones et al., "Low-Copy Plasmids can Perform as Well as or Better Than High-Copy Plasmids for Metabolic Engineering of Bacteria," *Metabolic Engineering* 2:328-338 (2000).
Lo et al., "Microbial engineering strategies to improve cell viability for biochemical production," *Biotechnology Advances* 31:903-914 (2013).
Murphy et al., "Combinatorial promoter design for engineering noisy gene expression," *PNAS* 104(31):12726-12731 (Jul. 31, 2007).
Peralta-Yahya et al., "Microbial engineering for the production of advanced biofuels," *Nature* 488:320-328 (Aug. 16, 2012).
Rubin, "Genomics of cellulosic biofuels," *Nature* 454:841-845 (Aug. 14, 2008).
Salis et al., "Automated design of synthetic ribosome binding sites to control protein expression," *Nature Biotechnology* 27(10):946-950 (7 pages) (Oct. 2009).
Tang et al., "Metabolic engineering for enhanced fatty acids synthesis in *Saccharomyces cerevisiae*," *Metabolic Engineering* 16:95-102 (2013).
Teo et al., "Bacterial FadR and synthetic promoters function as modular fatty acid sensor-regulators in *Saccharomyces cerevisiae*," *Eng. Life Sci.* 13:456-463 (2013).
Teo et al., "Development and Characterization of AND-Gate Dynamic Controllers With a Modular Synthetic GAL1 Core Promoter in *Saccharomyces cerevisiae*," *Biotechnology and Bioengineering* 111(1):144-151 (Jan. 2014).
Zhang et al., "Design of a dynamic sensor-regulator system for production of chemicals and fuels derived from fatty acids," *Nature Biotechnology* 30(4):354-359 (7 pages) (Apr. 2012).

* cited by examiner

*Primary Examiner* — Nancy A Treptow
(74) *Attorney, Agent, or Firm* — Seed IP Law Group LLP (57) ABSTRACT

The present invention relates to a nucleic acid molecule that comprises at least one synthetic GAL1 core promoter containing one or more ligand responsive operator sequences, preferably one or more FadR operator sites; at least one upstream enhancer element (UEE); and at least one nucleotide sequence encoding for one or more genes of interest; wherein the at least one synthetic GAL1 core promoter is operably linked to the at least one nucleotide sequence encoding for one or more genes of interest and the at least one UEE is operably linked to the at least one synthetic GAL1 core promoter. Also encompassed are expression systems and recombinant cells that include these nucleic acid molecules and methods that use these nucleic acid molecules, expression systems or cells.

20 Claims, 6 Drawing Sheets
Specification includes a Sequence Listing.

| DNA Part | Inclusive basepairs (5' of start codon) | Length (bp) | Reference |
|---|---|---|---|
| GAL1m* | -147 to -1 | 147 | This work |
| UEE (TEF1) | -401 to -198 | 204 | (Blazeck et al. 2012) |
| UEE (PGK1) | -982 to -152 | 831 | This work |
| UEE (HXT7) | -587 to -168 | 420 | This work |
| UEE (CUP1) | -456 to -143 | 314 | This work |
| UEE (PHO5) | -400 to -102 | 299 | This work |

Figure 6

| DNA Part | Seq ID No. | Sequence (5' to 3') *FadR operator sites shown in bold. |
|---|---|---|
| GAL1m* | 3 | TATATAAATGGATCTGCTATCTGGTACGACCAGATAATATCTGGTACGACCAGATTTTGTATTACTTCTATCTGGTACGACCAGATAGTATCAACAAAAAATTGTTAATATACCTCTATACTTTAACGTCAAGGAGAAAAAACTATA |
| UEE (TEF1) | 4 | ATGTTTCTACTCCTTTTTTACTCTTCCAGATTTTCTCGGACTCCGCGCATCGCCGTACCACTTCAAAACACCCAAGCACAGCATACTAAATTTCCCCTCTTTCTTCCTCTAGGGTGTCGTTAATTACCCGTACTAAAGGTTTGGAAAAGAAAAAAGAGACCGCCTCGTTTCTTTTTCTTCGTCGAAAAAGGCAATAAAAATTTT |
| UEE (PGK1) | 5 | GAAGTACCTTCAAAGAATGGGGTCTCATCTTGTTTTGCAAGTACCACTGAGCAGGATAATAATAGAAATGATAATATACTATAGTAGAGATAACGTCGATGACTTCCCATACTGTAATTGCTTTTAGTTGTGTATTTTTAGTGTGCAAGTTTCTGTAAATCGATTAATTTTTTTTTCTTTCCTCTTTTTATTAACCTTAATTTTTATTTTAGATTCCTGACTTCAACTCAAGACGCACAGATATTATAACATCTGCACAATAGGCATTTGCAAGAATTACTCGTGAGTAAGGAAAGAGTGAGGAACTATCGCATACCTGCATTTAAAGATGCCGATTTGGGCGCGAATCCTTTATTTTGGCTTCACCCTCATACTATTATCAGGGCCAGAAAAAGGAAGTGTTTCCCTCCTTCTTGAATTGATGTTACCCTCATAAAGCACGTGGCCTCTTATCGAGAAAGAAATTACCGTCGCTCGTGATTTGTTTGCAAAAAGAACAAAACTGAAAAAACCCAGACACGCTCGACTTCCTGTCTTCCTATTGATTGCAGCTTCCAATTTCGTCACACAACAAGGTCCTAGCGACGGCTCACAGGTTTTGTAACAAGCAATCGAAGGTTCTGGAATGGCGGGAAAGGGTTTAGTACCACATGCTATGATGCCCACTGTGATCTCCAGAGCAAAGTTCGTTCGATCGTACTGTTACTCTCTCTCTTTCAAACAGAATTGTCCGAATCGTGTGACAACAACAGCCTGTTCTCACACACTCTTTTCTTCTAACCAAGGGGGTGGTTTAGTTTAGTAGAACCTCGTGAAACTTACATTTACATA |
| UEE (HXT7) | 6 | CCGTGGAAATGAGGGGTATGCAGGAATTTGTGCGGGGTAGGAAATCTTTTTTTTTTTAGGAGGAACAACTGGTGGAAGAATGCCCACACTTCTCAGAAATGCATGCAGTGGCAGCACGCTAATTCGAAAAAATTCTCCAGAAAGGCAACGCAAAATTTTTTTTCCAGGGAATAAACTTTTTATGACCCACTACTTCTCGTAGGAACAATTTCGGGCCCCTGCGTGTTCTTCTGAGGTTCATCTTTTACATTTGCTTCTGCTGGATAATTTTCAGAGGCAACAAGGAAAAATTAGATGGCAAAAGTCGTCTTTCAAGGAAAAATCCCCACCATCTTTCGAGATCCCCTGTAACTTATTGGCAACTGAAAGAATGAAAAGGAGGAAAATACAAAATATACTAGAACTGAAAAAAAAAAAG |
| UEE (CUP1) | 7 | TCCCATTACCGACATTTGGGCGCTATACGTGCATATGTTCATGTATGTATCTGTATTTAAAACACTTTTGTATTATTTTTCCTCATATATGTGTATAGGTTTATACGGATGATTTAATTATTACTTCACCACCCTTTATTTCAGGCTGATATCTTAGCCTTGTTACTAGTTAGAAAAAGACATTTTTGCTGTCAGTCACTGTCAAGAGATTCTTTTGCTGGCATTTCTTCTAGAAGCAAAAGAGCGATGCGTCTTTTCCGCTGAACCGTTCCAGCAAAAAAGACTACCAACGCAATATGGATTGTCAGAATCA |
| UEE (PHO5) | 8 | TTTTCTTTGTCTGCACAAAGAAATATATATTAAATTAGCACGTTTTCGCATAGAACGCAACTGCACAATGCCAAAAAAAGTAAAAGTGATTAAAAGAGTTAATTGAATAGGCAATCTCTAAATGAATCGATACAACCTTGGCACTCACACGTGGGACTAGCACAGACTAAATTTATGATTCTGGTCCCTGTTTTCGAAGAGATCGCACATGCCAAATTATCAAATTGGTCACCTTACTTGGCAAGGCATATACCCATTTGGGATAAGGGTAAACATCTTTGAATTGTCGAAATGAAACG |

Figure 7

| Common name | Chemical structure | C:D |
|---|---|---|
| caprylic acid | $CH_3(CH_2)_6COOH$ | 8:0 |
| capric acid | $CH_3(CH_2)_8COOH$ | 10:0 |
| lauric acid | $CH_3(CH_2)_{10}COOH$ | 12:0 |
| myristic acid | $CH_3(CH_2)_{12}COOH$ | 14:0 |
| palmitic acid | $CH_3(CH_2)_{14}COOH$ | 16:0 |
| stearic acid | $CH_3(CH_2)_{16}COOH$ | 18:0 |
| arachidic acid | $CH_3(CH_2)_{18}COOH$ | 20:0 |
| behenic acid | $CH_3(CH_2)_{20}COOH$ | 22:0 |
| lignoceric acid | $CH_3(CH_2)_{22}COOH$ | 24:0 |
| cerotic acid | $CH_3(CH_2)_{24}COOH$ | 26:0 |

MODULAR SYNTHETIC GAL1 PROMOTER AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_501USPC_SEQUENCE_LISTING.txt. The text file is 4.5 KB, was created on Nov. 5, 2015, and is being submitted electronically via EFS-Web.

FIELD OF THE INVENTION

The invention relates to the formation of chimeric promoters suitable for use in expression systems controlling gene expression.

BACKGROUND OF THE INVENTION

Metabolic engineering of bio-catalytic cells with novel pathways require expression of one or more heterologous proteins. The introduction of new proteins for cellular synthesis increases the demand for cellular resources which can be detrimental to bio-catalytic cells. Constitutive expression of the novel pathway proteins can impede cell growth rates, which in turn reduces productivity. In addition, differing expression levels and activities of pathway enzymes can result in bottlenecks, which indicate wastage of cellular resources. Strategies for optimization of engineered pathways include static controls such as tuning of promoter strength, ribosome binding sites or copy number of the vector to enable balanced pathway reaction flux and remove bottlenecks, resulting in higher product yield.

Advanced optimization strategies involve dynamic controls where protein expression can be triggered on-demand. Dynamic control using inducible promoters enable the separation of growth phase from production phase, allowing cells to accumulate biomass before channeling resources for formation of desired chemicals. Furthermore, dynamic control via the sensing of key intermediates to regulate protein expression levels empowers the cell to, make real-time adjustments to its metabolic flux when host or environmental conditions change. This facilitates efficient consumption of cellular resources, with optimal protein expression levels at all times. The combination of dynamic control strategies by employing both inducible promoters and sensing-regulation can assist the engineering of bio-catalytic cells with robust cell growth and enhanced pathway productivity.

Concerns regarding energy security, petroleum supply and environmental protection have encouraged the development of advanced biofuels. Fatty acid derivatives, including fatty alcohols, fatty acid esters, alkenes and alkanes, are advanced biofuels as they have properties similar to fossil fuels and can be directly used in existing transportation infrastructure. One approach that has great potential for optimizing fatty acid derivatives producing yeast strains would involve dynamic controls. Coupling of the fatty acid sensor-regulator with an inducible promoter will enable AND-gate dynamic control, where the inducible promoter allows the production phase to be triggered when desired, and the sensor-regulator facilitates real-time metabolic flux corrections. In yeast, the galactose promoters which exhibit tight control and 1000 fold induction ratios are commonly employed as inducible promoters. However, for economically sustainable industrial production of fatty acid derived biofuels, the use of an affordable carbon source, such as lignocellulosic biomass is crucial. Since lignocellulose contains glucose, the galactose promoters are catabolite repressed, rendering them unsuitable for constructing the AND-gate dynamic controller. Hence, fatty acid sensor-regulation functionality needs to be introduced to inducible systems that function in glucose medium.

SUMMARY OF THE INVENTION

A first aspect of the invention relates to a nucleic acid molecule comprising:
(i) at least one synthetic GAL1 core promoter containing one or more ligand responsive operator sequences, preferably one or more FadR operator sites;
(ii) at least one upstream enhancer element (UEE); and
(iii) at least one nucleotide sequence encoding for one or more genes of interest;
wherein the at least one synthetic GAL1 core promoter is operably linked to the at least one nucleotide sequence encoding for one or more genes of interest and the at least one upstream enhancer element (UEE) is operably linked to the at least one synthetic GAL1 core promoter.

Another aspect of the invention relates to an expression system comprising one or more nucleic acid molecule as described herein.

In another aspect, the invention is directed to a recombinant cell comprising an expression system described herein.

In a still further aspect, the invention encompasses a method for recombinant expression of a gene product of interest, comprising cultivating the recombinant cell as described herein under conditions that allow the expression of a gene product of interest.

Other aspects of the invention will be apparent to a person skilled in the art with reference to the following drawings and description of various non-limiting embodiments.

BRIEF DESCRIPTION OF THE DRAWINGS

FIG. 1. (A) Schematic illustration of the synthetic hybrid promoters with upstream enhancer elements (UEEs) fused to the synthetic GAL1m* core promoter containing 3 tandem FadR operator sites. FadR repressors bind to the DNA operator sites to block transcription. Upon detection of fatty acids/fatty acyl-CoAs (FAs), the DNA binding activity of FadR is antagonized, triggering transcription of the downstream gene. (B) Synthetic hybrid promoters constructed include UEEs from constitutive (TEF1, PGK1 and HXT7), copper inducible (CUP1) and phosphate starvation inducible (PHO5) promoters. For hybrid promoters with constitutive UEEs, the transcription of yEGFP will be triggered by the detection of FAs. For CUP1-GAL1m*, both inducers $Cu^{2+}$ and FAs are needed to turn on yEGFP transcription. For PHO5-GAL1m*, yEGFP transcription will only trigger upon phosphate starvation and detection of FAs.

FIG. 6. DNA sequences of the hybrid promoter parts used. GAL1m* is the engineered synthetic GAL1 core promoter containing FadR operators while UEE stands for upstream enhancer elements.

DETAILED DESCRIPTION

The development and characterization of AND-gate dynamic controllers in *Saccharomyces cerevisiae* which combine two dynamic control strategies, inducible promoters and sensing-regulation is described. These dynamic controllers were constructed based on synthetic hybrid promoters. Promoter enhancer sequences were fused to a synthetic GAL1 core promoter containing DNA binding sites for the binding of a repressor that reduced DNA affinity upon interaction with key intermediates in a biochemical pathway. As fatty acids are key intermediates for production of fatty alcohols, fatty acid esters, alkenes, and alkanes, which are advanced biofuels, the fatty acid responsive FadR repressor and its operator sequence, were used to demonstrate the functionality of the dynamic controllers. A synthetic GAL1 core promoter was developed for use as a modular promoter part for constructing synthetic hybrid promoters and conferring fatty acid inducibility. The performance of the AND-gate dynamic controllers was demonstrated, where two inputs (fatty acid and copper presence/phosphate starvation) was required to switch the AND-gate ON.

Accordingly, in a first aspect the invention relates to a nucleic acid molecule comprising:
  (iv) at least one synthetic GAL1 core promoter containing one or more ligand responsive operator sequences, preferably one or more FadR operator sites;
  (v) at least one upstream enhancer element (UEE); and
  (vi) at least one nucleotide sequence encoding for one or more genes of interest;
wherein the at least one synthetic GAL1 core promoter is operably linked to the at least one nucleotide sequence encoding for one or more genes of interest and the at least one upstream enhancer element (UEE) is operably linked to the at least one synthetic GAL1 core promoter.

The term "nucleic acid" as used herein refers preferably to DNA. The nucleic acid molecule is preferably an artificially constructed nucleic acid molecule.

The term "synthetic GAL1 core promoter" refers to a promoter that has nucleic acid elements necessary for initiating transcription together with a ligand responsive operator. A core promoter includes the minimal portion of a promoter required to properly initiate transcription of a gene of interest. A core promoter generally includes a transcription start site, a binding site for RNA polymerase and a transcription factor binding site such as a TATA box. Preferably the at least one synthetic GAL1 core promoter comprises the nucleic acid sequence TATAAA (SEQ ID NO:2). The core promoter is preferably located upstream or 5' of the gene of interest transcribed as a result of the promoter core. In various embodiments the synthetic GAL1 core promoter is based on the GAL1 promoter originating from *Saccharomyces cerevisiae*.

In various embodiments the at least one synthetic GAL1 core promoter contains 2 or more, preferably 3 ligand responsive operator sites. An operator site includes a segment of the promoter sequence triggered by transcriptional regulators (ligand-controlled). These transcriptional regulators may be repressors, co-repressors or activators. Hence, depending on the type of ligand responsive operator site used the gene of interest will either be transcribed or have transcription blocked in the presence of the transcriptional regulator ligand. In various preferred embodiments the ligand responsive operator site comprises a FadR operator sites. The one or more FadR operator sites preferably confers fatty acid or fatty acyl-CoA regulation to the promoter more preferably the at least one ligand responsive operator site is a FadR operator site. Fatty acid repressor (FadR) operator sites confer fatty acid regulation to the promoter in systems expressing or containing FadR. FadR operator sites have been found in many organisms. FadR operator sites that originate from different species have different ligand sensitivities. A FadR operator site may originate from any suitable organism, preferably from a prokaryotic organism. In various embodiments the FadR operator site originates from *Escherichia coil* and/or *Vibrio cholerae*. In various embodiments each FadR operator site independently comprises or consists of the nucleic acid sequence ATCTGGTACGACCAGAT (SEQ ID NO:1).

In various embodiments the at least one synthetic GAL1 core promoter comprises or consists of the nucleic acid sequence set forth in SEQ ID NO:3; having at least 70, preferably at least 80, more preferably at least 90, most preferably at least 95% sequence identity with the nucleic acid sequence set forth in SEQ ID NO:3, optionally provided that said nucleic acid sequence comprises one or more FadR operator sites having the nucleic acid sequence set forth in SEQ ID NO:1 and/or a TATA-box sequence having the nucleic acid sequence set forth in SEQ ID NO:2.

The term "percent sequence identity" is taken to include a nucleic acid sequence having at least 70, 80 or 90% identical, preferably at least 95 or 98% identical at the nucleic acid level over at least 10, 20, 50, 100, 200 or 300 base pairs with the nucleic acid sequences within each alternative sequence. In particular, percent sequence identity should typically be considered with respect to those regions of the sequence known to be essential for the function of the promoter rather than non-essential neighboring sequences. Preferred nucleic acid of the invention comprise a contiguous sequence having greater than 60 or 70% identity, more preferably greater than 80 or 90% identity, to nucleic acid set forth in SEQ ID NO: 3.

Upstream enhancer elements (UEEs), control transcriptional frequency of a gene of interest. The UEE is generally located upstream or 5' of the core promoter and gene of interest to be transcribed. In various preferred embodiments the at least one upstream enhancer element is a constitutive enhancer element; an inducible enhancer element; or a non-catabolite repressed enhancer element.

As used here the term "catabolite" is a preferred energy source that can be used by a cell for growth and cell division. Common preferred sources of energy for cell growth and cell division include carbon based compounds such as glucose and galactose. Upstream enhancer elements that are catabolite repressed generally show inhibition of transcription of an associated gene in the presence of a preferred energy source. Hence, a non-catabolite repressed upstream enhancer element comprises an upstream enhancer element that is not inhibited in the presence of a preferred energy'source.

As eukaryotic promoters often contain two separate regions, the upstream enhancer elements (UEEs), which controls transcriptional frequency, and core elements, which determine the transcriptional direction and start site, in various embodiments various non-catabolite repressed UEEs were fused with a chimeric core promoter. Modularity of the chimeric core promoter for constructing hybrid promoters was demonstrated. Also shown was fusion of the synthetic GAL1 core promoter with various UEEs delivered synthetic hybrid promoters with inducible and AND-gate regulation properties.

In various embodiments the non-catabolite repressed upstream enhancer element comprises a constitutive enhancer. In various such embodiments the constitutive enhancer may be transcription enhancer factor 1 (TEF1) found in eukaryotes and may comprise a nucleic acid sequence set forth in SEQ ID NO. 4. Alternatively the constitutive enhancer may be phosphoglycerate kinase 1 (PGK1) found in eukaryotes and may comprise a nucleic acid sequence set forth in SEQ ID NO. 5. Alternatively the constitutive enhancer may be high-affinity hexose transporter 7 (HXT7) and may comprise a nucleic acid sequence set forth in SEQ ID NO. 6.

In various other embodiments the non-catabolite repressed upstream enhancer element comprises an inducible enhancer. In various such embodiments the inducible enhancer may be copper metallothionein (CUP1) inducible in the presence of copper. CUP1 may comprise a nucleic acid sequence set forth in SEQ ID NO. 7. Alternatively, the inducible enhancer may be repressible acid phosphatase (PHO5). PHO5 is strongly regulated in response to the level of inorganic phosphate (Pi) present in the growth medium whereby the absence of phosphates induces the PHO5 enhancer. The PHO5 enhancer may comprise a nucleic acid sequence set forth in SEQ ID NO. 8. Inducible enhances such as these have the added advantage of forming an AND-gate synthetic hybrid promoters that are regulated by both the levels of fatty acids and the inducing conditions of the enhancer element.

In various embodiments any two or three of the at least one synthetic GAL1 core promoter, the at least one upstream enhancer element and the at least one nucleotide sequence encoding for one or more genes of interest are not naturally associated with each other. The one or more ligand responsive operator sequences may originate from a prokaryotic organism. In various embodiments the FadR operator site may originate from *Escherichia coli* and/or *Vibrio cholerae*. In various embodiments the at least one synthetic GAL1 core promoter may originate from *Saccharomyces cerevisiae*.

Another aspect of the invention is an expression system comprising the nucleic acid molecule as described herein.

In various embodiments the expression system may be designed to operate in vitro or may be a cell based expression system. In a preferred embodiment, the expression system is a eukaryotic cell based system, preferably, the cell is a *Saccharomyces cerevisiae* cell. The construct may be an expression vector for expression of a protein encoded by a recombinant gene carried by said vector, a plasmid, cosmid, or artificial chromosome. A preferred vector is a vector that can self-replicate and express a given nucleic acid sequence included therein.

In various embodiments the one or more ligand responsive operator sequences confers fatty acid or fatty acyl-CoA regulation to the promoter. In various embodiments the one or more genes of interest comprising a nucleic acid sequence encoding a protein that modulates fatty acid or fatty acyl-CoA metabolism for production of fatty acid derivatives. Fatty acids are important sources of fuel because, when metabolized, they yield large quantities of ATP via beta oxidation catabolism. Similarly other lipolysis pathways are known in the art. Several anabolism pathways of fatty acids to form biological molecules are also known in the art.

Another aspect of the invention includes a recombinant cell comprising an expression system described herein.

The recombinant cell may be a cell-based expression system. In a preferred embodiment, the recombinant cell is a genetically engineered eukaryotic cell. In various embodiments the eukaryotic cell is a *Saccharomyces cerevisiae* cell.

Another aspect of the invention includes a method for the recombinant expression of a gene product of interest, comprising cultivating the recombinant cell as described herein under conditions that allow the expression of a gene product of interest. In various embodiments the gene product of interest is for the production of fatty acid derivatives.

In various embodiment's conditions that allow the expression of a gene product of interest for the production of fatty acid derivatives comprises the presence of a saturated fatty acid. Saturated fatty acids are long-chain carboxylic acids that usually have between 12 and 24 carbon atoms and have no double bonds. Thus, saturated fatty acids are saturated with hydrogen (since double bonds reduce the number of hydrogens on each carbon). Because saturated fatty acids have only single bonds, each carbon atom within the chain has 2 hydrogen atoms (except for the omega carbon at the end that has 3 hydrogens). Examples of saturated fatty acids include caprylic acid (C8), capric acid (C10), lauric acid (C12), myristic acid (C14), palmitic acid (C16), stearic acid (C18), arachidic acid (C20), behenic acid (C22), lignoceric acid (C24), and cerotic acid (C26). In various embodiment the saturated fatty acid is within the range of a 10 to 18 carbon saturated fatty acid, preferably within the range of a 12 to 16 carbon saturated fatty acid and most preferably a 14 carbon saturated fatty acid. In various embodiments the saturated fatty acid is selected from myristic acid, lauric acid and palmitic acid, most preferably, myristic acid.

In various embodiments, when the inducible enhancer element is copper metallothionein (CUP1) the conditions that allow the expression of a gene product of interest for the production of fatty acid derivatives comprise the presence of a fatty acid and the presence of copper.

In various embodiments when the inducible enhancer element is repressible acid phosphatase (PHO5) the conditions that allow the expression of a gene product of interest for the production of fatty acid derivatives comprise the presence of a fatty acid and the depletion of phosphates.

Other embodiments are within the following claims and non-limiting examples. It is to be understood that these examples are for illustrative purposes only and are not to be construed to limit the scope of the present invention.

Exemplary Embodiments

Described is a simple and convenient platform for constructing AND-gate dynamic controllers. As eukaryotic promoters contain two separate regions, the upstream enhancer elements (UEEs), which controls transcriptional frequency, and core elements, which determine the transcriptional direction and start site, various non-catabolite repressed UEEs were fused with a synthetic GAL1 core promoter containing 3 FadR operator sites, which confers fatty acid regulation to the promoter in yeast strains expressing FadR. Modularity of the synthetic GAL1 core promoter for constructing hybrid promoters was demonstrated. Also shown was fusion of this synthetic GAL1 core promoter with various UEEs delivered synthetic hybrid promoters with inducible and AND-gate regulation properties.

The modular synthetic GAL1 core promoter provides a simple platform for constructing AND-gate dynamic controllers, i.e. promoters that combine inducible functionality with regulation of protein expression levels upon detection of key intermediates towards the engineering and optimization of bio-catalytic yeast cells.

Introduction of DNA-binding operator sites into various core promoters will not be necessary as the use the modular synthetic GAL1 core promoter to introduce the operator sites is sufficient.

This method can also be applied to other ligand responsive DNA-binders, where their operator sequences can be introduced into synthetic GAL1 core promoters, in addition to heterologous expression of the DNA-binding protein.

Figure 1:
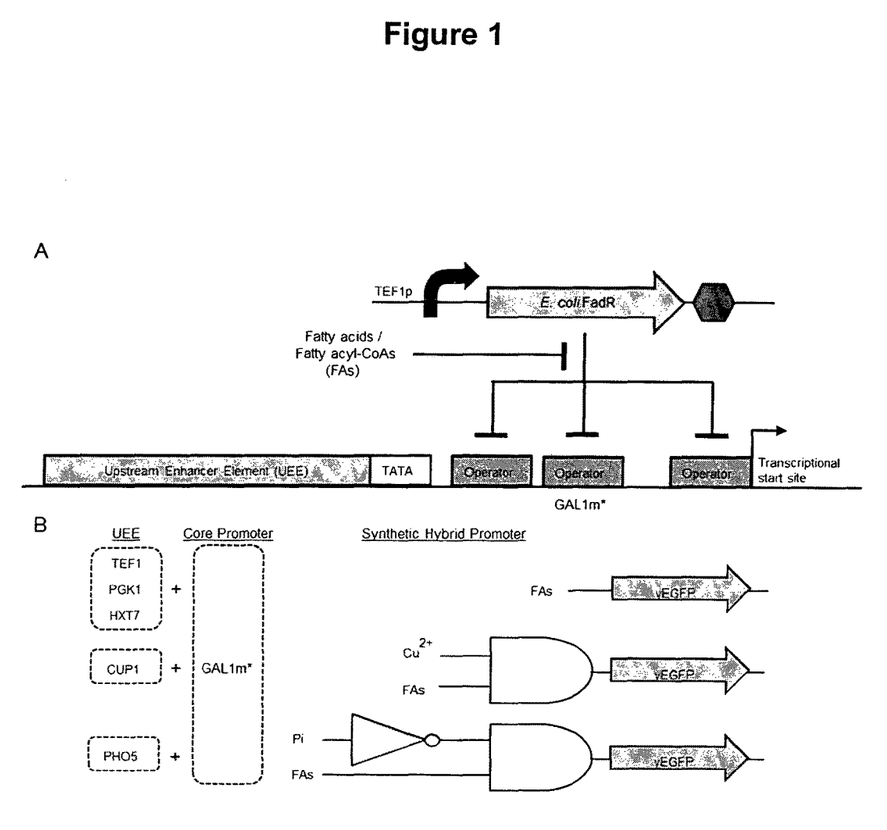
Figure 5:
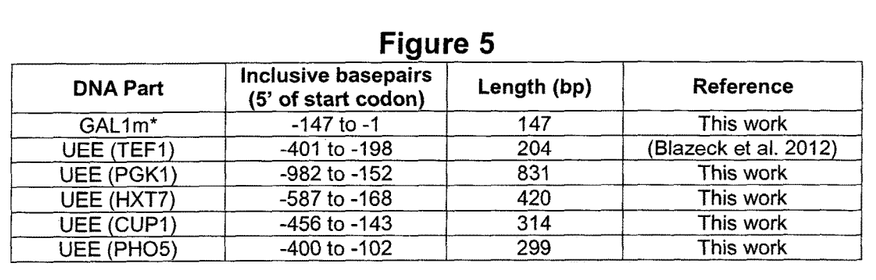
FIG. 5. List of synthetic hybrid promoter parts used in this study. GAL1m* is the engineered synthetic GAL1 core promoter containing FadR operators while UEE stands for upstream enhancer elements.

GAL1m*, which consists of the GAL1 core promoter region with 3 tandem repeats of FadR operator was used for fusion with various non-catabolite repressed UEEs to construct synthetic hybrid promoters. UEEs used include constitutive enhancers (TEF1, PGK1, HXT7)—which creates synthetic hybrid promoters that are regulated by the levels of fatty acids, and inducible enhancers (CUP1, PHO5)—which creates AND-gate synthetic hybrid promoters that are regulated by both the levels of fatty acids and the inducing conditions of the enhancer element (presence of copper for CUP1; absence of phosphates for PHO5) (FIG. 1). To select the UEE region, promoter sequences from the literature were used (Blazeck et al. 2012; Koller et al. 2000; Partow et al. 2010; Zhu and Zhang 1999), but removed sequences from the TATA box to the −1 of the start codon. Note that the GAL1m* core promoter includes the GAL1 TATA box. Details of the DNA sequences of the hybrid promoter parts used are listed in FIGS. 5 and 6.

Depicted in FIG. 1. (A) is a Schematic illustration of the synthetic hybrid promoters with upstream enhancer elements (UEEs) fused to the synthetic GAL1m* core promoter containing 3 tandem FadR operator sites. FadR repressors bind to the DNA operator sites to block transcription. Upon detection of fatty acids/fatty acyl-CoAs (FAs), the DNA binding activity of FadR is antagonized, triggering transcription of the downstream gene. (B) Synthetic hybrid promoters constructed include UEEs from constitutive (TEF1, PGK1 and HXT7), copper inducible (CUP1) and phosphate starvation inducible (PHO5) promoters. For hybrid promoters with constitutive UEEs, the transcription of yEGFP will be triggered by the detection of Fatty Acids. For CUP1-GAL1m*, both inducers $Cu^{2+}$ and Fatty Acids are needed to turn on yEGFP transcription. For PHO5-GAL1m*, yEGFP transcription will only trigger upon phosphate starvation and detection of Fatty Acids.

Figure 2:
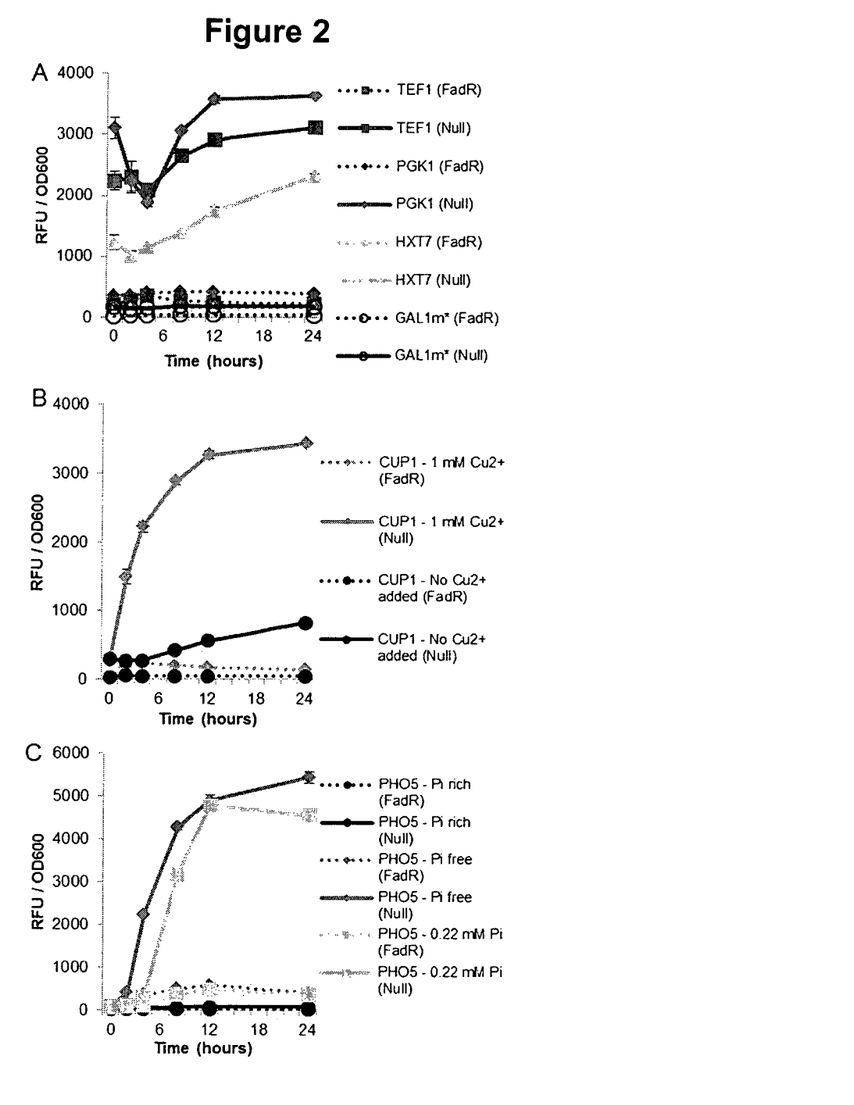
FIG. 2. Kinetic expression of the synthetic hybrid promoters in the presence (FadR) and absence (Null) of FadR. (A) Hybrid promoters with constitutive UEEs (TEF1-GAL1m*, PGK1-GAL1m* and HXT7-GAL1m*). GAL1m* is shown as a control containing no fused enhancers. (B) CUP1-GAL1m*. (C) PHO5-GAL1m*. Error bars represent standard deviation from 3 replicates.

To confirm the ability of the synthetic hybrid promoters for gene expression, the reporter protein, yEGFP was fused downstream of the promoters and the relative fluorescence units $(RFU)/OD_{600}$ were measured in the presence and absence of FadR repressors. RFU was normalized to the optical density to account for any difference in cell number. FIG. 2A shows the kinetic expression of the synthetic hybrid promoters with constitutive UEEs. In the absence of FadR, yEGFP expression was strong whereas in the presence of FadR, yEGFP expression was strongly repressed. For the synthetic hybrid promoters with inducible UEEs, the inducing conditions were triggered at time 0 and the kinetic response of the promoter was measured. FIG. 2B shows the hybrid CUP1-GAL1m* performance, where in the absence of FadR, strong yEGFP expression levels was quickly triggered upon the addition of 1 mM $Cu^{2+}$. In the presence of FadR, yEGFP expression was also triggered upon addition of 1 mM $Cu^{2+}$, but was significantly repressed by FadR. In the absence of $Cu^{2+}$, basal expression was observed from the CUP1-GAL1m* hybrid promoter in the strain without FadR expression. In the FadR expressing strain, basal expression was minimal. FIG. 2C shows the hybrid PHO5-GAL1m* promoter's kinetic expression. Here, 2 inducing conditions were used, first, the use of medium without any phosphates, and second, the use of a medium with a limited amount of phosphates (0.22 mM). In the strain containing no FadR repressors, strong yEGFP expression levels was observed 4 hours after the transfer of cells to growth medium containing no phosphates whereas in the presence of a low phosphates concentration (0.22 mM), yEGFP expression was delayed to 8 hours post transfer. This indicates temporal control of the promoter via growth medium nutrient adjustments. In the strain with FadR expressed, yEGFP expression was also triggered upon phosphate starvation, but was strongly repressed by FadR. In phosphate rich medium, basal expression from the PHO5-GAL1m* hybrid promoter was marginal. This result demonstrates the functionality of the hybrid promoters, where TEF1, PGK1, HXT7, CUP5 and PHO5 UEEs can enhance and regulate gene expression while the GAL1m* synthetic core promoter is effective as a modular core promoter to impart inducible fatty acid regulation.

Figure 3:
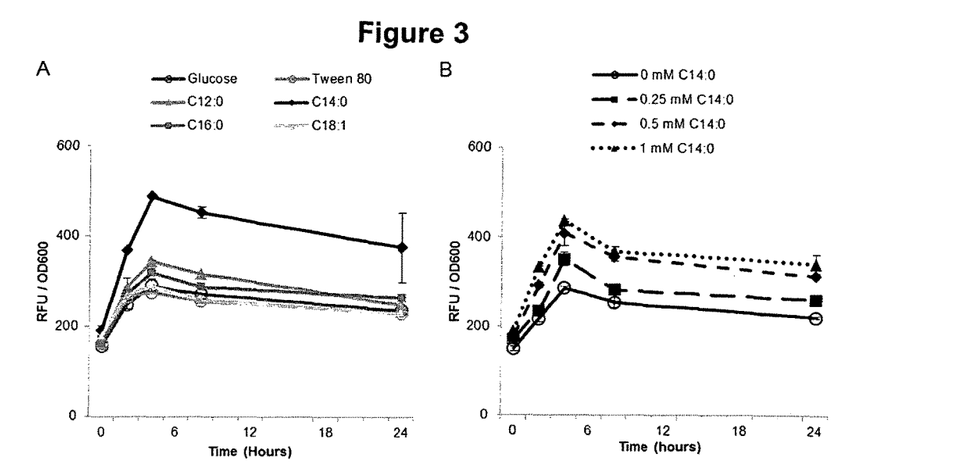
FIG. 3. Induction of the TEF1-GAL1m* synthetic hybrid promoter sensor system with (A) various chain length fatty acids. Cells were grown minimal medium with 1 mM of lauric acid (C12:0), myristic acid (C14:0), palmitic acid (C16:0) or oleic acid (C18:1). Cells were also grown in minimal medium without fatty acid addition (glucose) or with 0.5% Tween 80 as controls. (B) different concentrations of myristic acid (C14:0). Cells were grown in minimal medium with 0 (glucose), 0.25, 0.5 or 1 mM myristic acid. Error bars represent standard deviation from 3 replicates.
Figure 7:
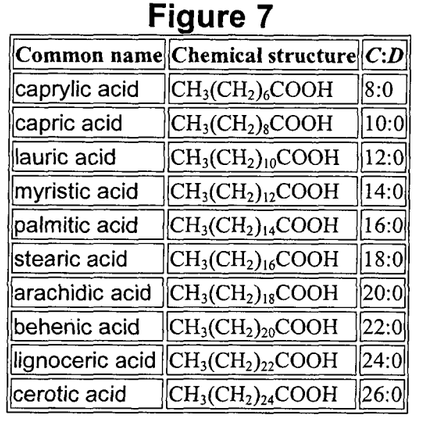
FIG. 7. Examples of Saturated Fatty Acids

Upon confirmation of good hybrid promoter capacity for protein expression, the ability of fatty acids to trigger an increase in yEGFP expression was tested. A TEF1-GAL1m* hybrid promoter was chosen to represent the constitutive UEEs and added various chain lengths fatty acids to the culture medium containing glucose as carbon source (FIG. 3A). Myristic acid (C14:0) was found to be the most effective inducer for triggering an increase in fluorescence signal. The effect of lauric acid (C12:0) and palmitic acid (C16:0) were small whereas oleic acid (C18:1) did not give higher yEGFP expression levels. In addition, the fatty acid sensor system was found to provide graded responses according to the concentrations of myristic acid added (FIG. 3B). Myristic acid, lauric acid (C12:0) and palmitic acid (C16:0) are all saturated fatty acids. Oleic acid is an unsaturated fatty acid. Examples of saturated fatty acids are listed in FIG. 7.

Figure 4:
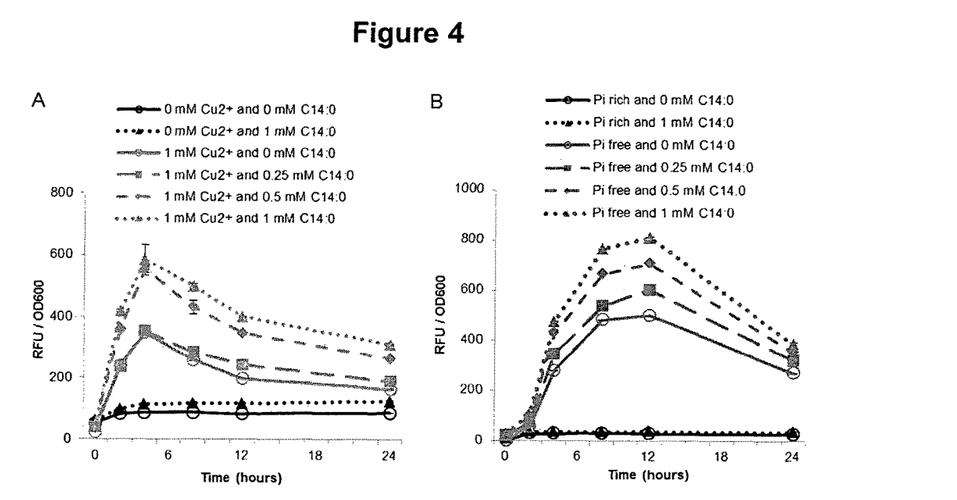
FIG. 4. Induction of the AND-gate dynamic controllers. (A) CUP1-GAL1m*. Cells were grown in minimal medium with 1 mM $Cu^{2+}$ and 0 (glucose), 0.25, 0.5 or 1 mM myristic acid. Cells were also grown in the absence of exogenously added $Cu^{2+}$ with 0 or 1 mM myristic acid. (B) PHO5-GAL1m*. Cells were grown in minimal medium without phosphates and 0 (glucose), 0.25, 0.5 or 1 mM myristic acid. Cells were also grown in phosphate rich medium with 0 or 1 mM myristic acid. Error bars represent standard deviation from 3 replicates.

The constructed AND-gate synthetic hybrid promoters were also characterized with a range of myristic acid inducers in the presence and absence of the UEE inducing conditions. For CUP1-GAL1m* (FIG. 4A), upon the addition of 1 mM $Cu^{2+}$, yEGFP expression was quickly triggered. Further addition of myristic acid resulted in increased RFU/OD$_{600}$, where higher myristic concentrations gave higher fluorescence levels. In the absence of exogenous Cu$^{2+}$, a basal expression was observed, and this basal level was increased slightly when myristic acid was added. For PHO5-GAL1m* (FIG. 4B), yEGFP expression was observed 4 hours after transfer of the cells to minimal medium without phosphates. The addition of a concentration range of myristic acids also resulted in graded RFU/OD$_{600}$ levels. In non-inducing conditions (phosphate-rich), basal expression was very low, and addition of myristic acids did not trigger increase in basal levels.

APPLICATIONS OF THE INVENTION

The modular synthetic GAL1 core promoter can be used as a modular part in the creation of synthetic biology parts for the creation of synthetic regulatory networks and dynamic controllers. By combining inducibility of an inducible promoter with sensor-regulation, this can assist the optimization of bio-catalysts for improved cell viability and pathway productivity. The use of FadR protein together with the synthetic hybrid promoters form AND-gate dynamic controllers that can be used to optimize yeast strains that produce fatty acid derivatives towards increased yield, titers and productivity.

By "comprising" it is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of". Thus, the phrase "consisting of" indicates that the listed elements are required or mandatory, and that no other elements may be present.

The inventions illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

By "about" in relation to a given numerical value, such as for temperature and period of time, it is meant to include numerical values within 10% of the specified value.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

REFERENCES

Blazeck J, Alper H S. 2013. Promoter engineering: Recent advances in controlling transcription at the most fundamental level. Biotechnology Journal 8(1):46-58.

Chen B, Ling H, Chang M W. 2013. Transporter engineering for improved tolerance against alkane biofuels in *Saccharomyces cerevisiae*. Biotechnology for Biofuels 6(1):21.

Hallenbeck P. 2012. Microbial Production of Fatty-Acid-Based Biofuels. In: Hallenbeck P C, editor. Microbial Technologies in Advanced Biofuels Production: Springer US. p 213-230.

Holtz W J, Keasling J D. 2010. Engineering Static and Dynamic Control of Synthetic Pathways. Cell 140(1):19-23.

Jones K L, Kim S-W, Keasling J D. 2000. Low-Copy Plasmids can Perform as Well as or Better Than High-Copy Plasmids for Metabolic Engineering of Bacteria. Metabolic Engineering 2(4):328-338.

Lo T-M, Teo W S, Ling H, Chen B, Kang A, Chang M W. 2013. Microbial engineering strategies to improve cell viability for biochemical production. Biotechnology Advances(0).

Peralta-Yahya P P, Zhang F, del Cardayre S B, Keasling J D. 2012. Microbial engineering for the production of advanced biofuels. Nature 488(7411):320-328.

Rubin E M. 2008. Genomics of cellulosic biofuels. Nature 454(7206):841-845.

Salis H M, Mirsky E A, Voigt C A. 2009. Automated design of synthetic ribosome binding sites to control protein expression. Nat Biotech 27(10):946-950.

Tang X, Feng H, Chen W N. 2013. Metabolic engineering for enhanced fatty acids synthesis in *Saccharomyces cerevisiae*. Metabolic Engineering 16(0):95-102.

Teo W S, Hee K S, Chang M W. 2013. Bacterial FadR and synthetic promoters function as modular fatty acid sensor-regulators in *Saccharomyces cerevisiae*. Engineering in Life Sciences.

Zhang F, Carothers J M, Keasling J D. 2012. Design of a dynamic sensor-regulator system for production of chemicals and fuels derived from fatty acids. Nat Biotech 30(4):354-359.

The invention claimed is:

1. A nucleic acid molecule comprising:
   (i) at least one synthetic GAL1 core promoter containing one or more ligand responsive operator sequences; wherein the one or more ligand responsive operator sequences comprise one or more FadR operator sites;
   (ii) at least one upstream enhancer element (UEE) selected from the group consisting of TEF1 (SEQ ID NO:4), PGK1 (SEQ ID NO:5), HXT7 (SEQ ID NO:6), CUP1 (SEQ ID NO:7) and PHO5 (SEQ ID NO:8); and
   (iii) at least one nucleotide sequence encoding for one or more genes of interest;

wherein the at least one synthetic GAL1 core promoter is operably linked to the at least one nucleotide sequence encoding for one or more genes of interest and the at least one upstream enhancer element (UEE) is operably linked to the at least one synthetic GAL1 core promoter.

2. The nucleic acid molecule of claim 1, wherein the at least one synthetic GAL1 core promoter contains 2 or more FadR operator sites.

3. The nucleic acid molecule of claim 1, wherein each of the one or more FadR operator sites independently comprises or consists of the nucleic acid sequence ATCTGGTACGACCAGAT (SEQ ID NO:1).

4. The nucleic acid molecule of claim 1, wherein the at least one synthetic GAL1 core promoter further comprises the nucleic acid sequence TATAAA (SEQ ID NO:2).

5. The nucleic acid molecule of claim 1, wherein the at least one synthetic GAL1 core promoter comprises or consists of the nucleic acid sequence:
   (i) set forth in SEQ ID NO:3; or
   (ii) having at least 70% sequence identity with the nucleic acid sequence set forth in SEQ ID NO:3, wherein the nucleic acid sequence comprises one or more FadR operator sites having the nucleic acid sequence set forth in SEQ ID NO:1 and/or a TATA-box sequence having the nucleic acid sequence set forth in SEQ ID NO:2.

6. The nucleic acid molecule of claim 1, wherein any two or three of the at least one synthetic GAL1 core promoter, the at least one upstream enhancer element and the at least one nucleotide sequence encoding for one or more genes of interest are not naturally associated with each other.

7. An expression system comprising the nucleic acid molecule of claim 1.

8. The expression system of claim 7, wherein the one or more FadR operator sites originate from a prokaryotic organism.

9. The expression system of claim 8, wherein the one or more FadR operator sites confer fatty acid or fatty acyl CoA regulation to the promoter.

10. The expression system of claim 8, wherein the one or more FadR operator sites originate from *Escherichia coli* and/or *Vibrio cholerae*.

11. The expression system of claim 7, wherein the at least one synthetic GAL1 core promoter originates from *Saccharomyces cerevisiae*.

12. The expression system of claim 7, wherein the one or more genes of interest comprises a nucleic acid sequence to encode a protein that modulates fatty acid or fatty acyl CoA metabolism for production of fatty acid derivatives.

13. A recombinant cell comprising an expression system according to claim 7.

14. The recombinant cell of claim 13, wherein the recombinant cell is a genetically engineered eukaryotic cell.

15. The recombinant cell of claim 14, wherein the genetically engineered eukaryotic cell is a *Saccharomyces cerevisiae* cell.

16. A method for the recombinant expression of a gene product of interest, comprising cultivating the recombinant cell of claim 13 under conditions that allow the expression of a gene product of interest.

17. The method of claim 16, wherein conditions that allow the expression of a gene product of interest comprises the presence of a saturated fatty acid.

18. The method of claim 17, wherein the saturated fatty acid is selected from myristic acid, lauric acid and palmitic acid.

19. The method of claim 16, wherein when the at least one upstream enhancer element comprises an inducible enhancer element set forth in SEQ ID NO:7, the conditions that allow the expression of a gene product of interest comprise the presence of fatty acids and the presence of copper.

20. The method of claim 16, wherein when the at least one upstream enhancer element comprises an inducible enhancer element set forth in SEQ ID NO:8, the conditions that allow the expression of a gene product of interest comprise the presence of fatty acids and the depletion of phosphates.

* * * * *

SEQUENCE LISTING

<160> NUMBER OF SEQ ID NOS: 8

<210> SEQ ID NO 1
<211> LENGTH: 17
<212> TYPE: DNA

```
<213> ORGANISM: Artificial Sequence
<220> FEATURE:
<223> OTHER INFORMATION: the FadR operator site may originates from
      Escherichia coli or Vibrio cholerae.

<400> SEQUENCE: 1
atctggtacg accagat                                                     17

<210> SEQ ID NO 2
<211> LENGTH: 6
<212> TYPE: DNA
<213> ORGANISM: Saccharomyces cerevisiae

<400> SEQUENCE: 2 tataaa                                                                  6

<210> SEQ ID NO 3
<211> LENGTH: 147
<212> TYPE: DNA
<213> ORGANISM: Artificial Sequence
<220> FEATURE:
<223> OTHER INFORMATION: core Gal promotor from Saccharomyces cerevisiae
      with FadR oporators from Escherichia coli and Vibrio cholerae
<220> FEATURE:
<221> NAME/KEY: misc_feature
<222> LOCATION: (19)..(35)
<223> OTHER INFORMATION: operator site
<220> FEATURE:
<221> NAME/KEY: misc_feature
<222> LOCATION: (39)..(55)
<223> OTHER INFORMATION: operator site
<220> FEATURE:
<221> NAME/KEY: misc_feature
<222> LOCATION: (70)..(86)
<223> OTHER INFORMATION: operator site

<400> SEQUENCE: 3
tatataaatg gatctgctat ctggtacgac cagataatat ctggtacgac cagattttgt       60
attacttcta tctggtacga ccagatagta tcaacaaaaa attgttaata tacctctata     120
ctttaacgtc aaggagaaaa aactata                                         147

<210> SEQ ID NO 4
<211> LENGTH: 204
<212> TYPE: DNA
<213> ORGANISM: Saccharomyces cerevisiae

<400> SEQUENCE: 4
atgtttctac tccttttta ctcttccaga ttttctcgga ctccgcgcat cgccgtacca       60
cttcaaaaca cccaagcaca gcatactaaa tttcccctct ttcttcctct agggtgtcgt     120
taattacccg tactaaaggt ttggaaaaga aaaagagac cgcctcgttt cttttctcc      180 gtcgaaaaag gcaataaaaa tttt                                           204

<210> SEQ ID NO 5
<211> LENGTH: 831
<212> TYPE: DNA
<213> ORGANISM: Saccharomyces cerevisiae

<400> SEQUENCE: 5
gaagtacctt caaagaatgg ggtctcatct tgttttgcaa gtaccactga gcaggataat       60
aatagaaatg ataatatact atagtagaga taacgtcgat gacttcccat actgtaattg     120
cttttagttg tgtattttta gtgtgcaagt ttctgtaaat cgattaattt ttttttcttt     180
cctcttttta ttaaccttaa tttttatttt agattcctga cttcaactca agacgcacag     240
```

| | |
|---|---|
| atattataac atctgcacaa taggcatttg caagaattac tcgtgagtaa ggaaagagtg | 300 |
| aggaactatc gcatacctgc atttaaagat gccgatttgg gcgcgaatcc tttattttgg | 360 |
| cttcaccctc atactattat cagggccaga aaaggaagt gtttccctcc ttcttgaatt | 420 |
| gatgttaccc tcataaagca cgtggcctct tatcgagaaa gaaattaccg tcgtcgtga | 480 |
| tttgtttgca aaagaacaa aactgaaaaa acccagacac gctcgacttc ctgtcttcct | 540 |
| attgattgca gcttccaatt tcgtcacaca acaaggtcct agcgacggct cacaggtttt | 600 |
| gtaacaagca atcgaaggtt ctggaatggc gggaaagggt ttagtaccac atgctatgat | 660 |
| gcccactgtg atctccagag caaagttcgt tcgatcgtac tgttactctc tctctttcaa | 720 |
| acagaattgt ccgaatcgtg tgacaacaac agcctgttct cacacactct tttcttctaa | 780 |
| ccaaggggt ggtttagttt agtagaacct cgtgaaactt acatttacat a | 831 |

<210> SEQ ID NO 6
<211> LENGTH: 420
<212> TYPE: DNA
<213> ORGANISM: Saccharomyces cerevisiae

<400> SEQUENCE: 6

| | |
|---|---|
| ccgtggaaat gaggggtatg caggaatttg tgcggggtag gaaatctttt ttttttttag | 60 |
| gaggaacaac tggtggaaga atgcccacac ttctcagaaa tgcatgcagt ggcagcacgc | 120 |
| taattcgaaa aaattctcca gaaaggcaac gcaaaatttt ttttccaggg aataaacttt | 180 |
| ttatgaccca ctacttctcg taggaacaat tcgggcccc tgcgtgttct tctgaggttc | 240 |
| atcttttaca tttgcttctg ctggataatt ttcagaggca acaaggaaaa attagatggc | 300 |
| aaaaagtcgt ctttcaagga aaaatcccca ccatctttcg agatcccctg taacttattg | 360 |
| gcaactgaaa gaatgaaaag gaggaaaata caaaatatac tagaactgaa aaaaaaaaag | 420 |

<210> SEQ ID NO 7
<211> LENGTH: 314
<212> TYPE: DNA
<213> ORGANISM: Saccharomyces cerevisiae

<400> SEQUENCE: 7

| | |
|---|---|
| tcccattacc gacatttggg cgctatacgt gcatatgttc atgtatgtat ctgtatttaa | 60 |
| aacacttttg tattattttt cctcatatat gtgtataggt ttatacggat gatttaatta | 120 |
| ttacttcacc acccttatt tcaggctgat atcttagcct tgttactagt tagaaaaaga | 180 |
| cattttgct gtcagtcact gtcaagagat tcttttgctg gcatttcttc tagaagcaaa | 240 |
| aagagcgatg cgtcttttcc gctgaaccgt tccagcaaaa aagactacca acgcaatatg | 300 |
| gattgtcaga atca | 314 |

<210> SEQ ID NO 8
<211> LENGTH: 299
<212> TYPE: DNA
<213> ORGANISM: Saccharomyces cerevisiae

<400> SEQUENCE: 8

| | |
|---|---|
| ttttctttgt ctgcacaaag aaatatatat taaattagca cgttttcgca tagaacgcaa | 60 |
| ctgcacaatg ccaaaaaaag taaagtgat taaaagagtt aattgaatag gcaatctcta | 120 |
| aatgaatcga tacaaccttg gcactcacac gtgggactag cacagactaa atttatgatt | 180 |

```
ctggtccctg ttttcgaaga gatcgcacat gccaaattat caaattggtc accttacttg        240
gcaaggcata tacccatttg ggataagggt aaacatcttt gaattgtcga aatgaaacg         299
```